(12) United States Patent
Lowenthal et al.

(10) Patent No.: US 11,997,991 B2
(45) Date of Patent: Jun. 4, 2024

(54) IMMUNE-ENHANCED AQUACULTURE

(71) Applicant: Atlantium Technologies Ltd, Beit-Shemesh (IL)

(72) Inventors: Assaf Lowenthal, Rehovot (IL); Tovit Litchi, Gedera (IL); Ytzhak Rozenberg, Caesarea (IL)

(73) Assignee: Atlantium Technologies Ltd., Beit-Shemesh (IL)

( * ) Notice: Subject to any disclaimer, the term of this patent is extended or adjusted under 35 U.S.C. 154(b) by 289 days.

(21) Appl. No.: 17/176,513

(22) Filed: Feb. 16, 2021

(65) Prior Publication Data
US 2021/0251196 A1    Aug. 19, 2021

Related U.S. Application Data

(60) Provisional application No. 62/977,423, filed on Feb. 17, 2020.

(51) Int. Cl.
| | |
|---|---|
| *A01K 61/13* | (2017.01) |
| *A61K 39/02* | (2006.01) |
| *A61K 39/245* | (2006.01) |
| *A61K 41/17* | (2020.01) |
| *A61P 31/22* | (2006.01) |

(52) U.S. Cl.
CPC ............ *A01K 61/13* (2017.01); *A61K 39/107* (2013.01); *A61K 39/245* (2013.01); *A61K 41/17* (2020.01); *A61P 31/22* (2018.01)

(58) Field of Classification Search
None
See application file for complete search history.

(56) References Cited

U.S. PATENT DOCUMENTS

| | | | |
|---|---|---|---|
| 9,809,467 | B2 | 11/2017 | Litchi et al. |
| 10,029,926 | B2 | 7/2018 | Litchi et al. |
| 10,294,124 | B2 | 5/2019 | Khan et al. |
| 10,427,954 | B2 | 10/2019 | Vardiel et al. |
| 2018/0044204 | A1* | 2/2018 | Lichi ................. A61L 2/10 |

FOREIGN PATENT DOCUMENTS

WO    WO 2017/118989    7/2017

OTHER PUBLICATIONS

Itami et al. Journal of Aquatic Animal Health 1:3 (1989) 238-242, (Year: 1989).*
Allam et al., Journal of Invertebrate pathology, vol. 131, pp. 121-136, 2015. (Year: 2015).*
Rodriguez et al. Advances in Virology Research vo. 62, 2003 p. 113. (Year: 2003).*
Wang et al. Emerging Viral Disease of Fish and Shrimp, Issue Infect, Dis. Bsel, Karger, vol. 4 pp. 35-58, 2007. (Year: 2007).*
Guerrero Migel Effect_of_Low_Pressure_and_Medium_Press . . . pdf (Year: 2019).*
Itami, T., Y. Takahashi, and Y. Nahamura. "Efficacy of vaccination against vibrosis in cultured kuruma prawns *Penaeus japonicus*." Journal of Aquatic Animal Health 1.3 (1989): 238-242 Itami et al Sep. 1, 1989.
PCT Search Report For Application No. PCT/IL2021/050176, dated Jun. 9, 2021.
Valero Y et al, Vaccination with UV-inactivated nodavirus partly protects European sea bass against infection, while inducing few changes in immunity, Developmental and Comparative Immunology 86 (2018) 171-179, https://doi.org/10.1016/j.dci.2018.05.013.
Melillo D et al, Front. Immunol., Aug. 22, 2018 Sec. Cytokines and Soluble Mediators in Immunity vol. 9—2018 | https://doi.org/10.3389/fimmu.2018.01915.
Zhang T et al, The specifically enhanced cellular immune responses in Pacific oyster (*Crassostrea gigas*) against secondary challenge with Vibrio splendidus, Developmental & Comparative Immunology vol. 45, Issue 1, Jul. 2014, pp. 141-150, https://doi.org/10.1016/j.dci.2014.02.015.
McKay D et al, Immunity in the invertebrates, Immunology. Jul. 1969; 17(1): 127-137.
Hick P et al, Stability of Ostreid herpesvirus-1(OsHV-1) and assessment of disinfection of seawater and oyster tissues using a bioassay. Aquaculture450(2016)412-421, http://dx.doi.org/10.1016/j.aquaculture.2015.08.025.
Delisle L et al, Inactivated ostreid herpesvirus-1 induces an innate immune response in the Pacific oyster, *Crassostrea gigas*, hemocytes, Front Immunol. 2023; 14: 1161145. Published online Apr. 28, 2023. doi: 10.3389/fimmu.2023.1161145.

* cited by examiner

*Primary Examiner* — Jana A Hines
*Assistant Examiner* — Khatol S Shahnan Shah
(74) *Attorney, Agent, or Firm* — PEARL COHEN ZEDEK LATZER BARATZ LLP

(57) ABSTRACT

Aquaculture systems and methods are provided, as well as immunogenic compositions and methods of immunologically protecting bivalves against specified pathogens. Methods include inactivating specified pathogens using UV (ultraviolet) radiation, exposing invertebrates grown or to be grown in aquaculture to the specified UV-inactivated pathogens to enhance an immune reaction of the exposed invertebrates toward the specified pathogens, and growing the exposed invertebrates in aquaculture. For example, the methods were demonstrated to increase the immune response of oysters to ostreid herpesvirus 1 (OsHV-1) following their prior exposure to UV-inactivated OsHV-1.

12 Claims, 7 Drawing Sheets

200

210 Inactivating specified pathogens using UV (ultraviolet) radiation

212 Irradiating the specified pathogens with UV radiation to yield an immunogenic composition

214 Inactivating the pathogens in a static setting using collimated UV radiation

216 Inactivating the pathogens in a dynamic setting, applying UV radiation to a flow carrying the pathogens

220 Exposing invertebrates grown or to be grown in aquaculture to the UV-inactivated pathogens to enhance their immune reaction

222 Exposing bivalves to the immunogenic composition to enhance their immune reaction toward the specified pathogens

224 Injecting the immunogenic composition to the invertebrates

226 Adding the immunogenic composition into water in which the invertebrates are held and/or grown

228 Exposing the invertebrates to the immunogenic composition repeatedly

230 Growing the exposed invertebrates in aquaculture

*Figure 2*

IMMUNE-ENHANCED AQUACULTURE

CROSS REFERENCE TO RELATED APPLICATIONS

This application claims from the benefit U.S. Provisional Application No. 62/977,423, filed on Feb. 17, 2020, which is incorporated herein by reference in its entirety.

BACKGROUND OF THE INVENTION

1. Technical Field

The present invention relates to the field of invertebrate aquaculture, and more particularly, to enhancing the immunity of grown invertebrate to pathogens.

2. Discussion of Related Art

Invertebrates grown in aquaculture are susceptible to a variety of waterborne pathogens. Bivalves, as filtering organisms, are especially susceptible. In contrast to vertebrates however, invertebrates lack an adaptive immune response and do not produce antibodies.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a method comprising: inactivating specified pathogens using UV (ultraviolet) radiation, exposing invertebrates grown or to be grown in aquaculture to the specified UV-inactivated pathogens to enhance an immune reaction of the exposed invertebrates toward the specified pathogens, and growing the exposed invertebrates in aquaculture.

One aspect of the present invention provides an aquaculture system comprising: an immunization unit configured to expose invertebrates to specified UV-inactivated pathogens to enhance an immune reaction of the exposed invertebrates toward the specified pathogens, an aquaculture growth unit configured to grow the exposed invertebrates, and possibly a pathogen-inactivation unit configured to inactivate specified pathogens using UV radiation.

One aspect of the present invention provides an immunogenic composition comprising inactivated OsHV-1 (ostreid herpesvirus 1) and/or inactivated *Vibrio* bacteria, produced by irradiating the OsHV-1 viruses and/or the *Vibrio* bacteria with UV radiation.

One aspect of the present invention provides a method of immunologically protecting bivalves against specified pathogens, the method comprising irradiating the specified pathogens with UV radiation to yield an immunogenic composition, and exposing the bivalves to the immunogenic composition to enhance their immune reaction toward the specified pathogens.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 2 is a high-level flowchart illustrating a method, according to some embodiments of the invention.

DETAILED DESCRIPTION OF THE INVENTION

Figure 1A:
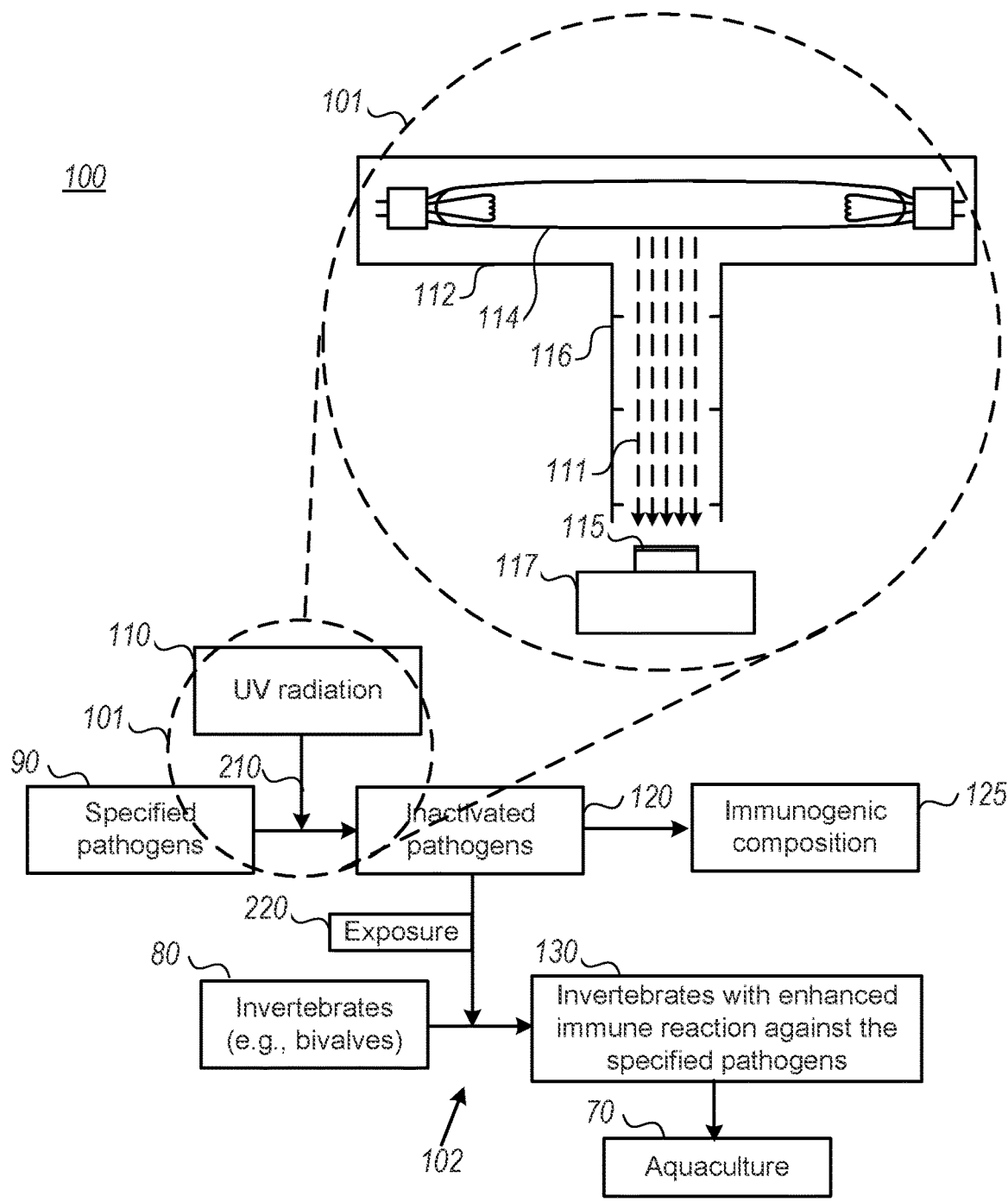
FIGS. 1A, 1D and 1E are high-level schematic block diagrams of aquaculture systems, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Embodiments of the present invention provide efficient and economical methods and mechanisms for improving the immunity of invertebrates against pathogens and thereby provide improvements to the technological field of aquaculture. Surprisingly, the it has been found that it is possible to inactivate pathogens and use them in vaccine-like approaches in invertebrates. For example, in bivalves, it was shown that the innate immune system of bivalves could be enhanced to develop a certain degree of memory, and consequently, immune protection against pathogen. As an example, UV radiation was used to inactivate important pathogens for the bivalve aquaculture industry, OsHV-1

(ostreid herpesvirus 1) as a virus representative and *Vibrio splendidus* as a bacterium representative, and have shown the inactivated pathogens to be immunostimulants in *Crassostrea gigas* (the Pacific oyster) and *Mytilus galloprovincialis* (the Mediterranean mussel), respectively. Other invertebrates for which immune response may be enhanced in the disclosed manner include other mollusks, arthropods such as the crustacean shrimps, prawn and crabs, and cephalopods such as squid, echinoderms such as sea cucumbers and sea urchins. In certain embodiments, disclosed systems and methods may be applied in fish aquaculture, enhancing the immune response of the fish against pathogens such as viruses and bacteria.

Table 1 provides non limiting examples for invertebrates and vertebrates (fish) and their respective pathogens, which may be handled by disclosed systems and methods applying UV-inactivation of the pathogens to enhance the immune reaction of the respective invertebrates and vertebrates (fish).

in Table 1, by irradiating the specified pathogens with UV radiation to yield an immunogenic composition, and exposing the fish to the immunogenic composition to enhance their immune reaction toward the specified pathogens.

Aquaculture systems and methods are provided, as well as immunogenic compositions and methods of immunologically protecting bivalves against specified pathogens. Methods include inactivating specified pathogens using UV (ultraviolet) radiation, exposing invertebrates grown or to be grown in aquaculture to the specified UV-inactivated pathogens to enhance an immune reaction of the exposed invertebrates toward the specified pathogens, and growing the exposed invertebrates in aquaculture. In a non-limiting example, the methods were demonstrated to increase the immune response of oysters to OsHV-1 following their prior exposure to UV-inactivated OsHV-1.

Figure 1B:
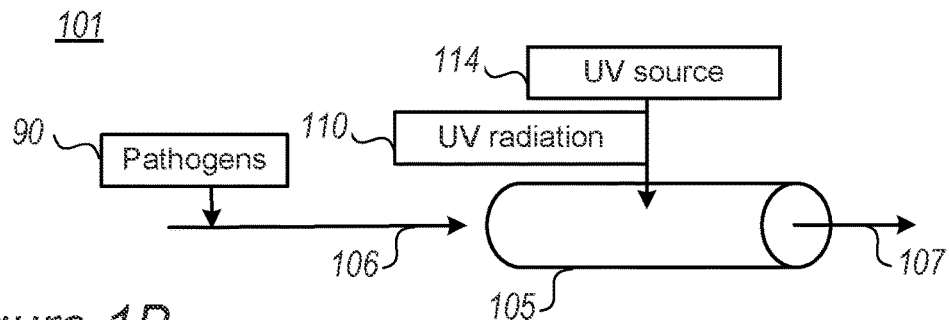
FIGS. 1B and 1C are high-level schematic illustrations of pathogen-inactivation units, according to some embodiments of the invention.
Figure 1C:
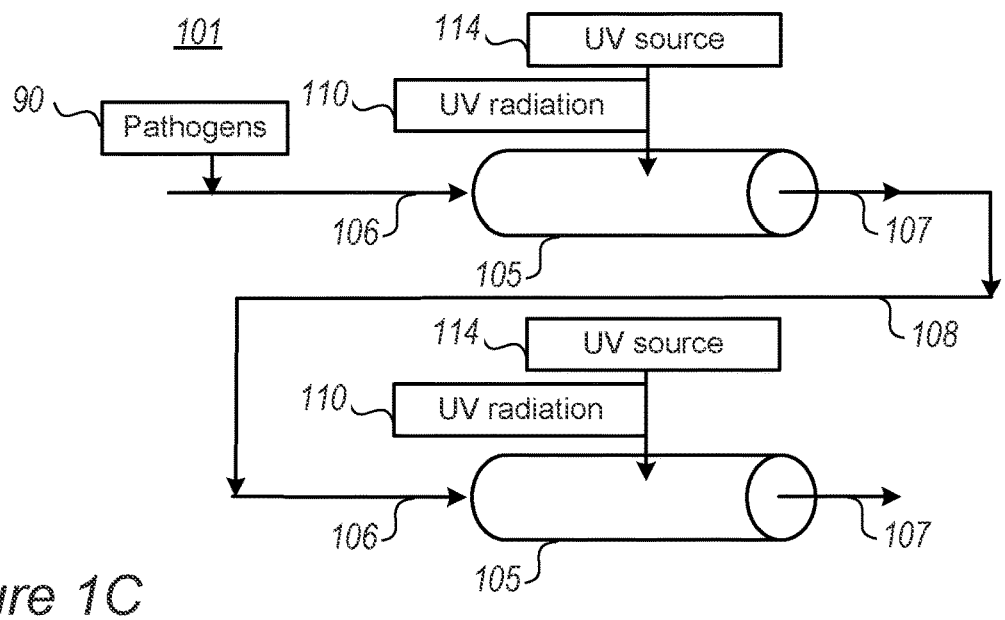
Figure 1D:
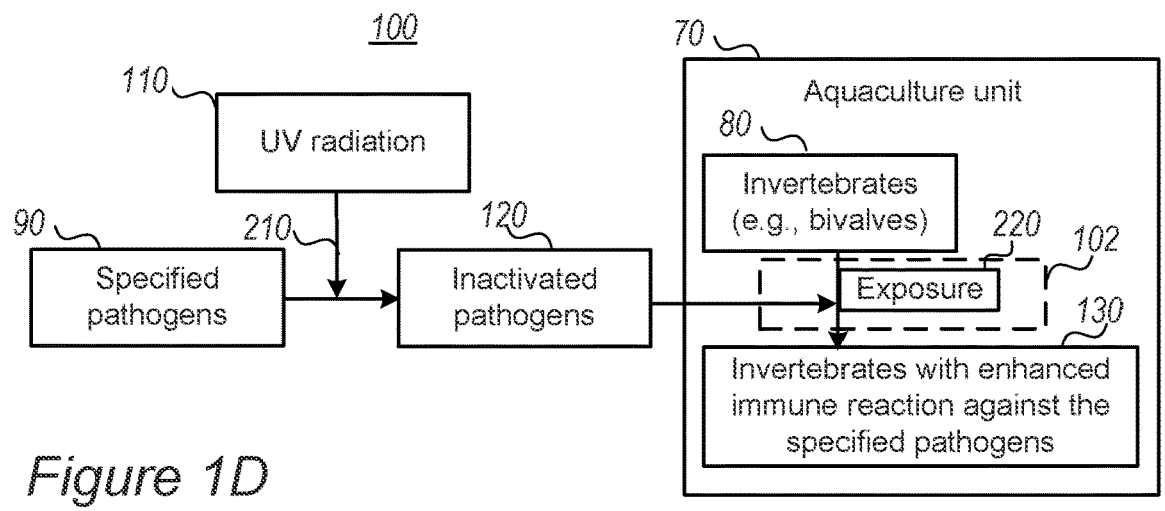
Figure 1E:
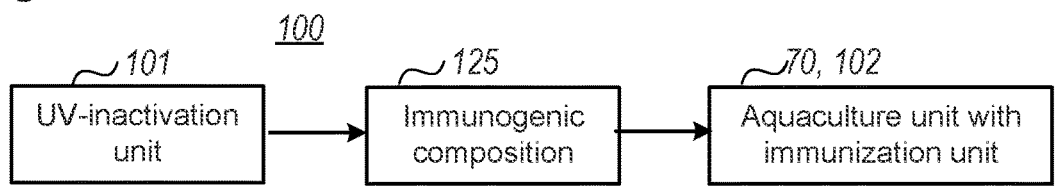

FIGS. 1A, 1D and 1E are high-level schematic block diagrams of aquaculture systems 100, according to some embodiments of the invention. FIGS. 1B and 1C are high-level schematic illustrations of pathogen-inactivation units

TABLE 1

Organisms (invertebrates and vertebrates) and their respective pathogens, which may be UV-inactivated to enhance immunity of the organisms grown in aquaculture.

| Host organism in aquaculture | Disease | Pathogen to be UV-inactivated |
|---|---|---|
| Abalone (sea snail) (*Haliotis laevigata*, *H. rubra*) | AVG-Abalone Viral Ganglioneuritis | AbHV (Abalone Herpes Virus) |
| Shrimp/Prawns, e.g., *Litopenaeus vannamei*, *Penaeus monodon* and others Shrimps: | IHHN-Infectious Hypodermal and Haematopoitic Necrosis | IHHNV |
| *Penaeus monodon* and others *Penaeid shrimps* | Yellowhead disease Infectious myonecrosis | Yellow head virus (YHV) IMNV (infectious myonecrosis virus) |
| Shrimp: *Macrobrachium rosenbergii* | White tail disease | MrNV (Macrobrachium rosenbergii nodavirus) |
| Shrimps: *Litopenaeus vannamei* and others | Taura syndrome | Taura syndrome virus (TSV) |
| Shrimps: *Litopenaeus vannamei* and others | WSS (White spot syndrome) | WSSV |
| Squid, mackerel, tuna, sardines, crab, conch, shrimp, and bivalves, such as oysters and clams. | Acute hepatopancreatic necrosis | Vibrio parahaemolyticus |

Certain embodiments comprise inactivating specified pathogens using UV radiation, exposing vertebrates such as fish, grown or to be grown in aquaculture, to the specified UV-inactivated pathogens to enhance an immune reaction of the exposed vertebrates (e.g., fish) toward the specified pathogens, and growing the exposed vertebrates (e.g., fish) in aquaculture.

Certain embodiments comprise an aquaculture system comprising an immunization unit configured to expose vertebrates such as fish to specified UV-inactivated pathogens to enhance an immune reaction of the exposed vertebrates (e.g., fish) toward the specified pathogens, an aquaculture growth unit configured to grow the exposed vertebrates (e.g., fish), and possibly a pathogen-inactivation unit configured to inactivate specified pathogens using UV radiation.

Certain embodiments comprise immunogenic compositions comprising inactivated pathogens that are listed in Table 1, produced by irradiating the respective pathogens with UV radiation.

Certain embodiments comprise methods of immunologically protecting fish against specified pathogens listed, e.g.,

101, according to some embodiments of the invention. In various embodiments, system 100 comprises pathogen-inactivation unit 101 configured to inactivate (stage 210, see below) specified pathogens 90 using UV radiation 110 and/or an immunization unit 102 configured to expose (stage 220, see below) invertebrates 80 to specified UV-inactivated pathogens 120 and/or to an immunogenic composition 125—to enhance an immune reaction of the exposed invertebrates toward the specified pathogens 130. System 100 may further comprise an aquaculture growth unit 70 configured to grow exposed invertebrates 130—with higher yields due to their increased immune reaction.

FIG. 1A schematically illustrates UV inactivation by a UV source 114 such as a low pressure and/or medium pressure UV lamp 114 within a lamp enclosure 112 attached to a collimating tube 116 configured to yield collimated radiation 111 that is applied to sample 115. In certain embodiments, UV radiation may be carried out by one or more UV sources 114 such as low pressure and/or medium pressure UV lamp(s), LEDs (light emitting diodes), or any other UV source. The type of UV source 114 may be selected according to the required wavelengths. UV radiation may comprise radiation within the wavelength range of 200-400 nm, and may have peaks e.g., at any of 253.5 nm, 265 nm, 275 nm (e.g., ±5 nm, ±10 nm, ±15 nm, ±20 nm, or intermediate values) and e.g., at peak widths of e.g., ±5 nm, ±10 nm, ±15 nm, ±20 nm, or intermediate values).

In certain embodiments, UV inactivation may be carried out on flowing water containing the respective pathogens (see, e.g., FIG. 1B below), and may involve a variety of optical configurations that are arranged to ensure inactivation of the pathogens. In certain embodiments, a large quantity of UV inactivated pathogens 120 may be prepared in pathogen-inactivation unit 101 (e.g., as an immunogenic composition 125 comprising UV-inactivated pathogens 120 and possibly additives, see example below) and then added gradually or in one or more portions to immunization unit 102 and/or directly to aquaculture growth unit 70 to yield the enhanced immune resistance to specified pathogens 90.

It is noted that immunogenic composition 125 may be prepared separately, e.g., in in pathogen-inactivation unit 101 that operates independently of immunization unit 102. For example, immunogenic composition 125 may be prepared prior to the operation of immunization unit 102, and be added to it (and/or to aquaculture growth unit 70) during their operation. Decoupling pathogen-inactivation unit 101 and immunization unit 102 may be advantageous in certain operation schemes, using immunogenic composition 125 (possibly with additives, conservatives etc.) as intermediate material that can be used to generate the immunity in the grown organisms.

In various embodiments, exposure 220 of invertebrates 80 to UV-inactivated pathogens 120 may be carried out by direct injection and/or by introduction of UV-inactivated pathogens 120 into the water in which invertebrates 80 are held and/or grown. Exposure 220 may be carried out in separate container(s) and/or in aquaculture growth unit 70, as disclosed below. Exposure 220 of invertebrates 80 to UV-inactivated pathogens 120 may be carried out during larval and/or adult stages of invertebrates 80. It is noted that the term "water" used herein refers to any water-based liquid used in aquaculture practice, e.g., water with additives. It is emphasized that disclosed UV-inactivation 210 may be configured to maintain whatever pathogen structures are required to initiate the immune response in invertebrates 80, e.g., cell membranes or other cell structures, specific proteins or other molecular structures, specific genome parts, etc.

FIGS. 1B and 1C illustrate schematically pathogen-inactivation units 101 configured to operate on flowing water, receiving an incoming flow 106 (into which pathogens 90 may be introduced), applying UV radiation 110 to the flow in a conduit 105—to yield outcoming flow 107 with UV-inactivated pathogens. It is noted that UV-inactivation 210 may be carried out on static water (as illustrated schematically in FIG. 1A, possibly using a shutter to define the exposure duration and a stirrer to mix the water) and/or on flowing water (as illustrated schematically in FIGS. 1B and 1C), according to specific requirements. Applying UV radiation 110 to the flow in conduit 105 may be carried out in various configurations of unit 101, e.g., as disclosed in any of U.S. Pat. Nos. 9,809,467, 10,029,926, 10,294,124 and 10,427,954 incorporated herein by reference in their entirety. For example, UV radiation 110 may be collimated to yield a uniform radiation distribution and/or conduit 105 may be configured to provide internal reflection (e.g., total internal reflection) to uniformly distribute the UV radiation within the water flowing therethrough, ensuring uniform and/or effective UV-activation of the pathogens in flow 106. In certain embodiments, UV LEDs may be positioned at locations along conduit 105 that provide a uniform UV radiation distribution. In certain embodiments, the UV radiation distribution can be non-uniform but predictable in the sense that a specified threshold of pathogen-inactivation may be ensured.

The dose and time of exposure may be determined with respect to the volume of the container in static UV irradiation units 101 and/or with respect to the conduit dimensions and flow velocity in dynamic UV irradiation units 101, in relation to the UV transmission of the water. In certain embodiments, the dimension of the container and duration of retention of the water in static units 101 and/or the conduit dimensions and flow velocity in dynamic UV irradiation units 101 may be selected according to specified throughput and time requirements. For example, when using collimated UV radiation 110, the UV dose may be determined by Equation 1:

$$D_{CB} = E_s P_s (1-R) \frac{L}{d+L} \frac{1-10^{-(A_{WL}d)}}{A_{WL}d \ln(10)} \quad \text{Equation 1}$$

with $D_{CB}$ denoting the UV dose (mJ/cm$^2$), Es denoting the average UV intensity (measured before and after irradiating the sample) (mW/cm$^2$), $P_f$ denoting the Petri factor (unitless), R denoting the reflectance at the air-water interface at 254 nm (unitless), as an example for the applied wavelength, L denoting the distance from the centerline of the lamp (e.g., in embodiments such as illustrated in FIG. 1A) to the suspension surface (cm), d denoting the depth of the suspension of the pathogens in the water (cm), AWL denoting the UV absorbance at the specific used wavelength (unitless) and t denoting the exposure time (s).

In certain embodiments, pathogen-inactivation unit 101 may be configured to comprise at least one flow loop 108, as illustrated schematically in FIG. 1C, delivering outcoming flow 107 back to conduit 105 and/or to other irradiated conduit(s) as incoming flow 106 to apply UV radiation 110 in a stepwise manner. In certain embodiments, the water may be circulated through same conduit 105 to apply UV radiation 110 multiple times, possibly with intermediate mixing. Using smaller UV doses, the recurring irradiation may provide average uniform pathogen UV-inactivation.

FIGS. 1D and 1E illustrate schematically aquaculture systems 100 in which the immunization of the grown invertebrates is carried out at least partly within aquaculture growth unit 70. In such embodiments, immunization unit 102 (indicated schematically within aquaculture growth unit 70) may be a separate compartment within aquaculture unit 70 and/or the immunization may be carried within aquaculture growth unit 70 as a whole.

In certain embodiments, pathogen-inactivation unit 101 may be adjacent to aquaculture unit 70, with immunization unit 102 being part of aquaculture unit 70, as illustrated schematically in FIG. 1D. For example, pathogens 90 may be introduced to the inlet into aquaculture unit 70 and undergo UV inactivation immediately prior to the entrance of the water into aquaculture unit 70, so that the enhancing of the immune reaction of the invertebrates to the pathogen may be carried out within aquaculture unit 70 itself. In certain embodiments, illustrated e.g., in FIG. 1E Immunogenic composition 125 may be prepared separately and introduced into aquaculture unit 70 (and/or into immunization unit 102 therewithin) on one or more occasions. For example, portions of immunogenic composition 125 may be added to aquaculture unit 70 periodically, possibly corresponding to growth stages of invertebrates grown therewithin.

Elements from FIGS. 1A-1E may be combined in any operable combination, and the illustration of certain elements in certain figures and not in others merely serves an explanatory purpose and is non-limiting.

FIG. 2 is a high-level flowchart illustrating a method 200, according to some embodiments of the invention. The method stages may be carried out with respect to system 100 described above, which may optionally be configured to implement method 200. Method 200 may comprise the following stages, irrespective of their order.

Method 200 may comprise inactivating specified pathogens using UV radiation (stage 210), exposing invertebrates grown or to be grown in aquaculture to the specified UV-inactivated pathogens (stage 220) to enhance an immune reaction of the exposed invertebrates toward the specified pathogens, and growing the exposed invertebrates in aquaculture (stage 230). For example, method 200 may be used as method 200 of immunologically protecting bivalves against specified pathogens, comprising: irradiating the specified pathogens with UV radiation to yield an immunogenic composition (stage 212), and exposing the bivalves to the immunogenic composition to enhance their immune reaction toward the specified pathogens (stage 222), followed by growing the exposed bivalves in aquaculture (stage 230).

In various embodiments, inactivation 210 of the specified pathogens may be carried out in a static setting using collimated UV radiation (stage 214) and/or inactivation 210 of the specified pathogens may be carried out in a dynamic setting, applying UV radiation to a flow carrying the pathogens (stage 216)—for example by delivering uniform UV radiation to a conduit supporting the flow. In certain embodiments, applying UV radiation to a flow carrying the pathogens may be carried out by delivering UV radiation repeatedly to one or more conduits supporting the flow and comprising at least one flow loop.

In various embodiments, exposing 220 of the invertebrates to the specified UV-inactivated pathogens may be carried out by injecting an immunogenic composition comprising the specified UV-inactivated pathogens to the invertebrates (stage 224) and/or by adding the immunogenic composition into water in which the invertebrates are held and/or grown (stage 226), possibly repeatedly (stage 228) to maintain a required immunity level and/or to parallel developmental stage of the invertebrates, providing immunity to consecutive generations and/or developmental stages.

Certain embodiments comprise immunogenic composition 125 comprising inactivated OsHV-1 (ostreid herpesvirus 1) and/or inactivated *Vibrio* bacteria, produced by irradiating 212 the OsHV-1 viruses and/or the *Vibrio* bacteria with UV radiation 110.

The following experimental data illustrates the efficiency of disclosed systems, methods and composition in enhancing the immune response of *Crassostrea gigas* (the Pacific oyster) to OsHV-1, using UV-inactivated pathogens.

Figure 3A:
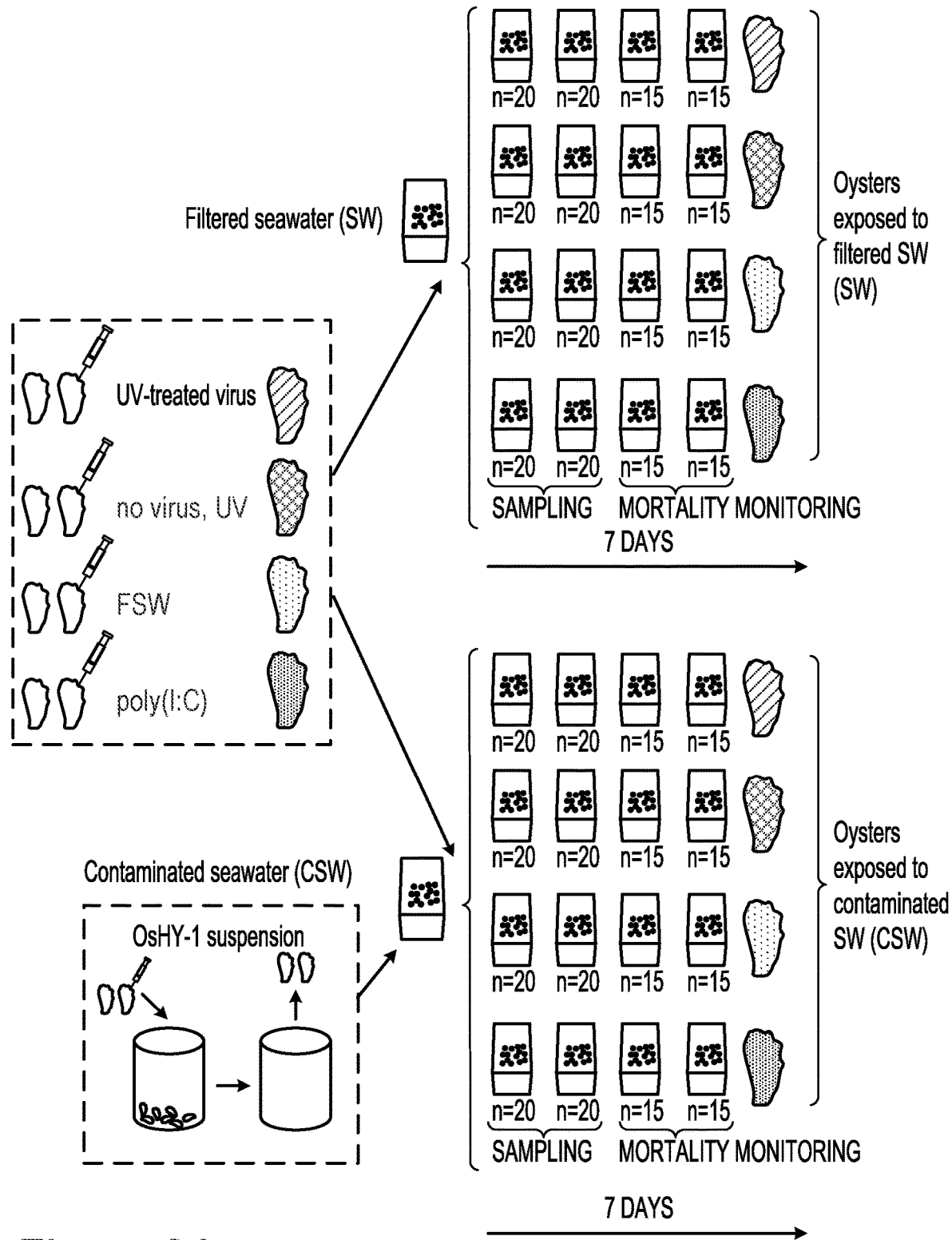
FIGS. 3A-3C illustrate the setting and results of experiments conducted to show the enhancing the immune response of *C. gigas* to OsHV-1 using UV-inactivated pathogens, according to some embodiments of the invention.
Figure 3B:
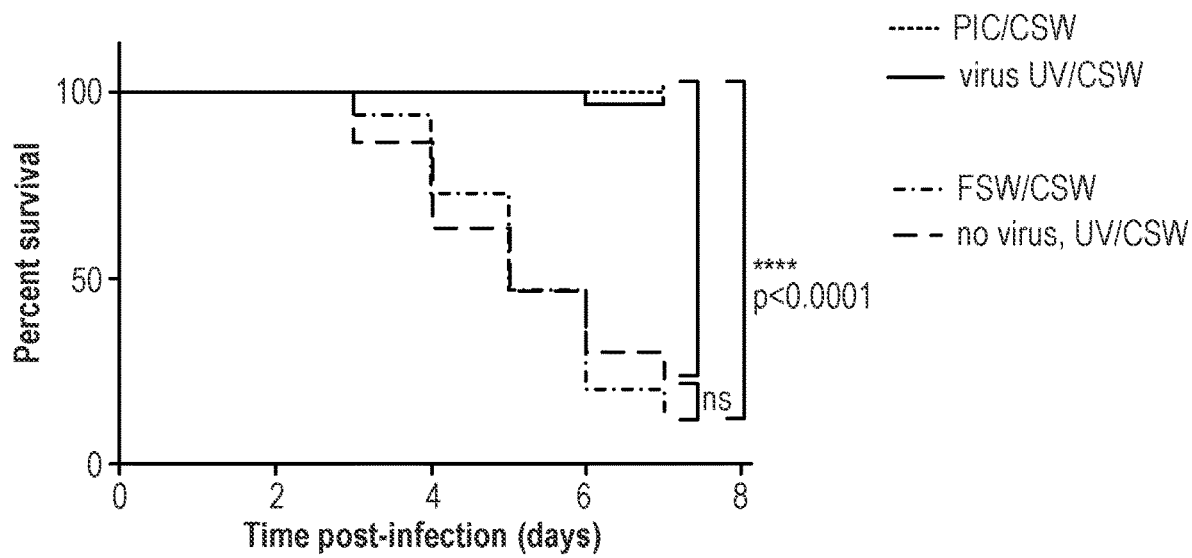
Figure 3C:
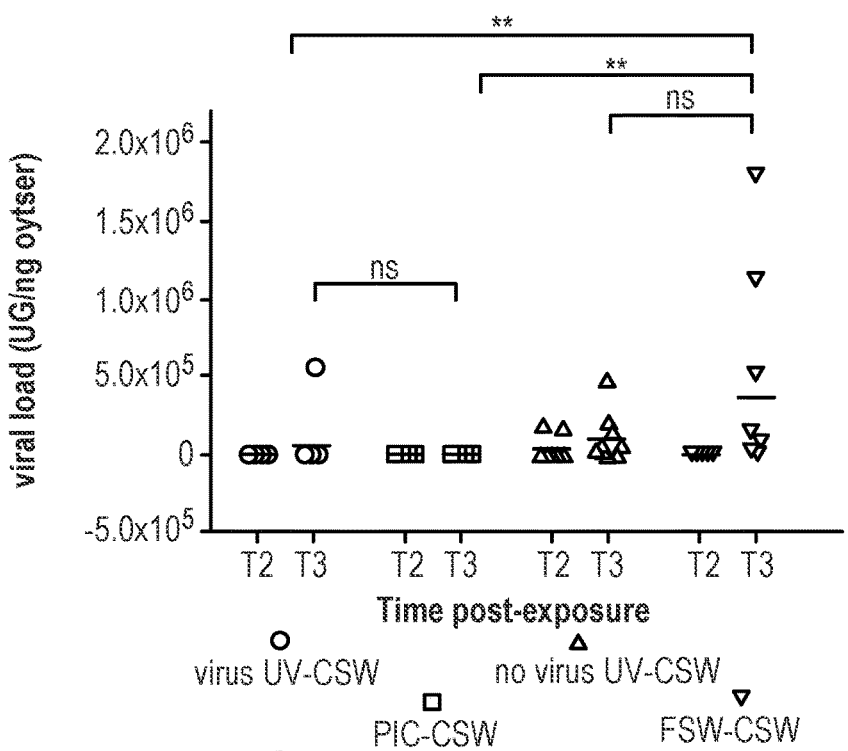

FIGS. 3A-3C illustrate the setting and results of experiments conducted to show the enhancing the immune response of *C. gigas* to OsHV-1 using UV-inactivated pathogens, according to some embodiments of the invention. FIG. 3A illustrate schematically the experimental setting and FIGS. 3B and 3C provide corresponding experimental results.

As illustrated schematically in FIG. 3A, four sets of virus treatments were checked on the oysters that were grown without and with exposure to the active viruses. Specifically, the four treatments included (i) UV-treated OsHV-1, (ii) UV-treated non-viral suspension as a negative control (denoted "no virus, UV"), (iii) filtered seawater as a negative control (denoted "FSW") and (iv) Poly (I:C), indicating virus-mimic synthetic double stranded RNA (dsRNA) which is known to be a key signature of viral infection and widely used as a viral mimic in vertebrates—as a positive control (denoted "PIC"). The UV treatment in (i) and (ii) were carried out for 105 seconds using low pressure UV as illustrated schematically in FIG. 1A. UV inactivation was carried out by a low pressure UV mercury arc lamp 114 within lamp enclosure 112 attached to collimating tube 116 configured to yield collimated radiation 111 (e.g., at 254 nm wavelength)—that is applied to sample 115, placed on a magnetic stiffer 117. It is noted that this experimental setting is not limiting, and that various system configuration may be used, as illustrated, e.g., in any combination of features from FIGS. 1A-1E discussed above.

Each of the treatments was applied by injection to n=140 oysters, which were then split into two groups, with 70 oysters each. One group was exposed to filtered seawater (four treatments+SW) and the other group was exposed to OsHV-1 contaminated seawater (four treatments+CSW)—with the number of oysters in each sub-group shown in FIG. 3A. In each group of 70 oysters, 40 oysters were used for sampling and 30 oysters were used for mortality monitoring. OsHV-1 contaminated seawater was prepared by infecting healthy oysters with 100 μL of OsHV-1 and using the water they were in after 24 h as CSW. All sub-groups were held under similar conditions and were sampled every day for 8 days. FIG. 3B illustrates the survival rates of the eight subgroups during the experiment, in the CSW group, and FIG. 3C illustrated the viral load of oysters in the sub-groups at T2, denoting samples taken 24 hours after the exposure to SW/CSW and at T3, denoting samples taken 48 hours after the exposure to SW/CSW, in the CSW group.

As seen in FIG. 3B, while the negative controls (treatments (ii) and (iii)) resulted in declining oyster populations in contaminated seawater (CSW), reaching 23% and 13% survival 7 days post-infection, respectively—UV-treated OsHV-1 (treatment (i)) demonstrated significant (****p<0.0001) higher survival rates than the negative controls (FSW-CSW), with 96.7% survival 7 days post-infection, and similar results to treatment (iv) with poly(I:C), with 100% survival 7 days post-infection, no significant differences between treatments (i) and (iv).

As seen in FIG. 3C, while the negative controls (treatments (ii) and (iii)) reached high viral loads 48 hours after infection in CSW ($4.8·10^5$ and $1.8·10^6$ genome units/extract DNA, respectively)—UV-treated OsHV-1 (treatment (i)) demonstrated significantly lower viral loads (p-value<0.05, mean load $5.6·10^4$ genome unit/extract DNA) which were similar to treatment (iv) with poly(I:C) with a mean viral load of $1.73·10^2$, with no significant differences between treatments (i) and (iv) 48 hours after infection in CSW.

Figure 4:
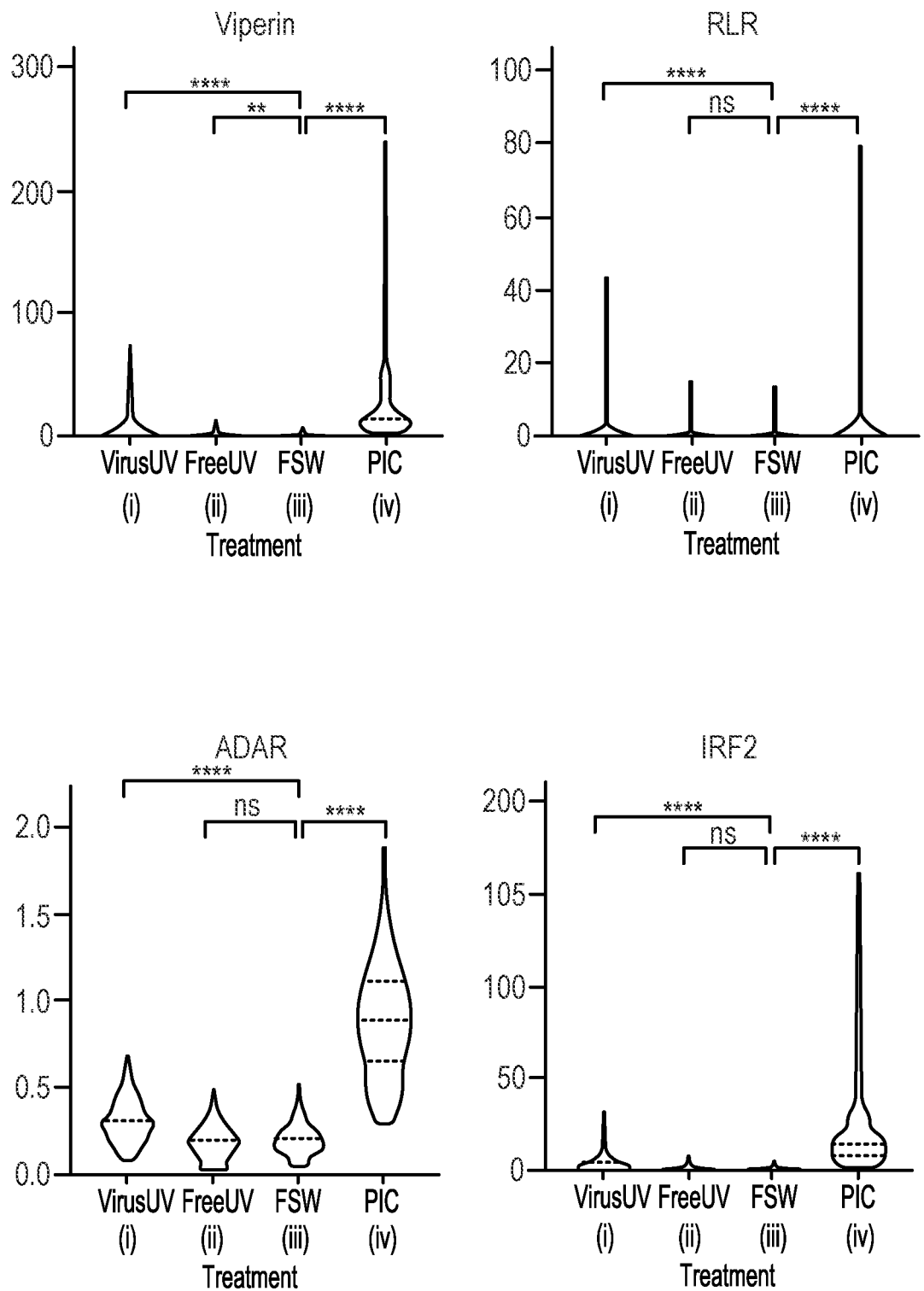
FIG. 4 illustrates the effect of treatments (i) to (iv) on the expression of each of the eight genes presented in Table 2.
Figure 4:
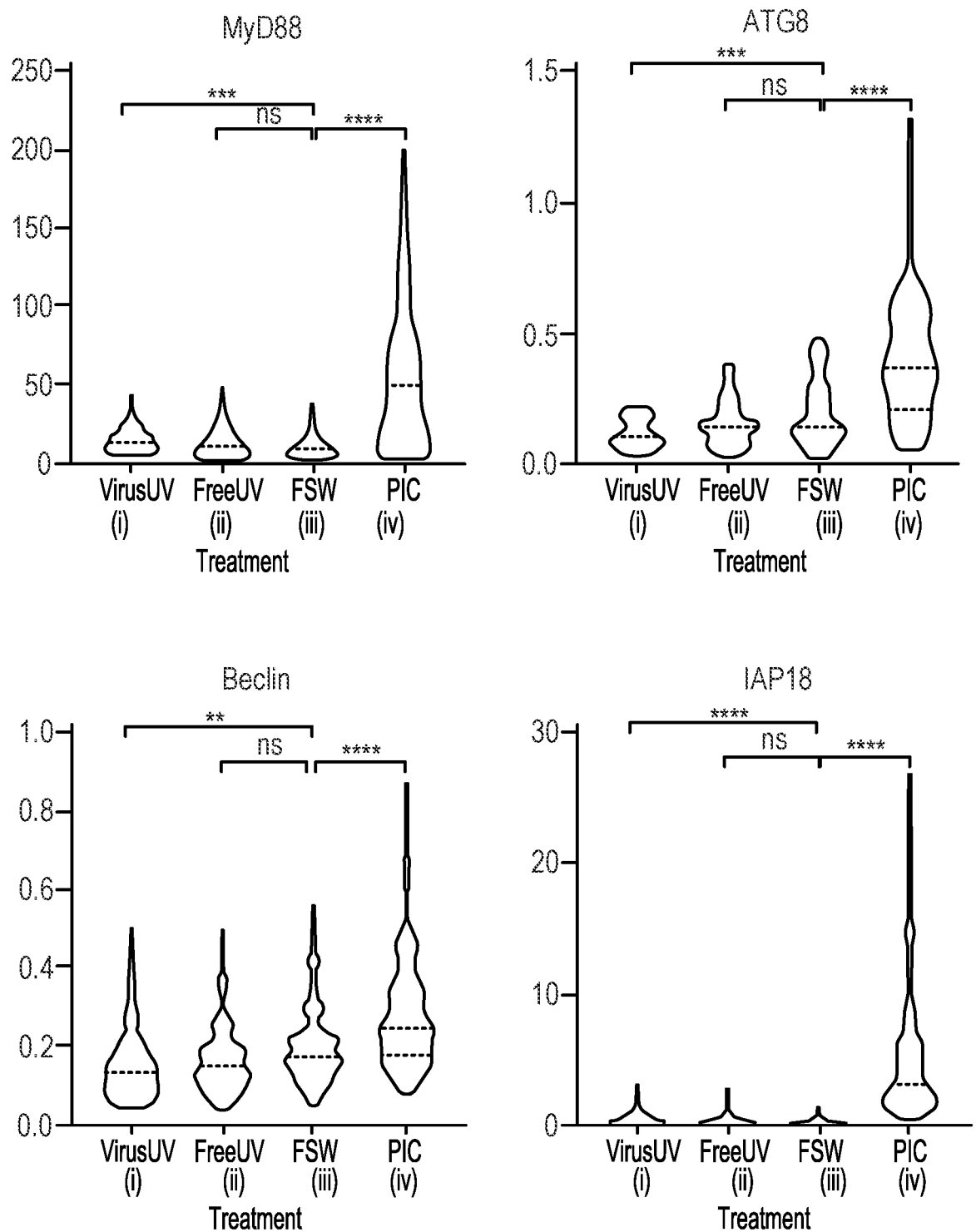

It has been further found out that disclosed methods yield activation of antiviral immune genes in *C. gigas*, as illustrated in Table 2 and FIG. 4. Table 2 provides the relative expression levels for eight candidate immune/cell death genes under treatment conditions (i) through (iv)—24 hours after treatment with respect to naive oysters. Candidate genes were chosen according to the literature, as belonging to (a) the interferons and NF-κB pathways: RLR (RIG-I-like receptor gene, MyD88-1 (Myeloid differentiation factor 88-1, which is a TLR adaptor protein), IRF-2 (interferon regulation factor 2, transcription factor); (b) antiviral effectors-:ADAR (adenosine deaminase, RNA specific, antiviral effector), viperin (antiviral effector), IAP (inhibitor of apoptosis proteins) and (c) the autophagy pathway: ATG8 (Autophagy-related protein 8), Beclin-1 (autophagy regulation). The results show that UV-inactivated virus exposure induced an upregulation of antiviral genes (except for ADAR) and autophagy-related genes, similar but to a lesser extent than for the positive control treatment (iv) of exposure to poly(I:C).

TABLE 2 relative expression levels of eight immune genes to the four treatments

| Treatment | Viperin | RLR | ADAR | IRF2 | MyD88-1 | ATG8 | Beclin | IAP18 |
|---|---|---|---|---|---|---|---|---|
| (i) Virus, UV | 9.3 | 3.1 | 0.3 | 5.1 | 16.8 | 0.1 | 0.2 | 0.6 |
| (ii) Only UV | 1.9 | 0.7 | 0.3 | 0.8 | 13.5 | 0.2 | 0.2 | 0.4 |
| (iii) FSW | 0.9 | 0.8 | 0.3 | 0.6 | 11.6 | 0.2 | 0.2 | 0.3 |
| (vi) Poly (I:C) | 28.6 | 4.5 | 0.9 | 23.9 | 59.2 | 0.4 | 0.3 | 4.8 |

Values above 1 indicate up-regulation of the gene 24 h after exposure, values between 0.5-1 indicate stable expression of the respective gene and values under 0.5 indicate down-regulation of the respective gene.

FIG. 4 illustrates the effect of treatments (i) to (iv) on the expression of each of the eight genes presented in Table 2. FIG. 4 provides violin plots of the expression patterns for the eight candidate genes, under treatments (i) through (iv). Significance of the differences between the treatments was evaluated using Dunn's Multiple Comparison Test; ns >0.05, $p<0.01$, *$p<0.001$, ****$p<0.0001$. This more detailed presentation of the gene activation results corroborates the disclosed action mechanism of exposure to UV-inactivated viruses.

To conclude, the results demonstrate that disclosed exposure of invertebrates to UV-inactivated pathogens enhance their immune response toward these pathogens and improve aquaculture practice.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:
   inactivating specified pathogens using UV (ultraviolet) radiation,
   exposing invertebrates grown or to be grown in aquaculture to the specified UV-inactivated pathogens to enhance an immune reaction of the exposed invertebrates toward the specified pathogens, and
   growing the exposed invertebrates in aquaculture.

2. The method of claim 1, wherein the exposing of the invertebrates to the specified UV-inactivated pathogens is carried out by injecting an immunogenic composition comprising the specified UV-inactivated pathogens to the invertebrates.

3. The method of claim 1, wherein the exposing of the invertebrates to the specified UV-inactivated pathogens is carried out by adding the immunogenic composition into water in which the invertebrates are held and/or grown.

4. The method of claim 3, wherein the adding of the immunogenic composition is carried out repeatedly.

5. The method of claim 1, wherein the inactivation of the specified pathogens is carried out in a static setting using collimated UV radiation.

6. The method of claim 1, wherein the inactivation of the specified pathogens is carried out in a dynamic setting, applying UV radiation to a flow carrying the pathogens.

7. The method of claim 6, wherein the inactivation of the specified pathogens is carried out by delivering uniform UV radiation to a conduit supporting the flow.

8. The method of claim 6, wherein the inactivation of the specified pathogens is carried out by delivering UV radiation repeatedly to one or more conduits supporting the flow and comprising at least one flow loop.

9. The method of claim 1,
   wherein the invertebrates are bivalves and the method comprises immunologically protecting the bivalves against the specified pathogens,
   wherein the inactivating comprises irradiating the specified pathogens with UV radiation to yield an immunogenic composition, and
   wherein the growing of the exposed invertebrates in aquaculture comprises exposing the bivalves to the immunogenic composition to enhance their immune reaction toward the specified pathogens.

10. The method of claim 9, wherein the inactivated specified pathogens comprise inactivated OsHV-1 (ostreid herpesvirus 1).

11. The method of claim 1,
   wherein the invertebrates are shrimps or prawns and the method comprises immunologically protecting the shrimps or prawns against the specified pathogens, wherein the inactivating comprises irradiating the specified pathogens with UV radiation to yield an immunogenic composition, and wherein the growing of the exposed invertebrates in aquaculture comprises exposing the shrimps or prawns to the immunogenic composition to enhance their immune reaction toward the specified pathogens.

12. The method of claim 11, wherein the shrimps or prawns comprise at least one of: *Litopenaeus vannamei, Penaeus monodon* or other penaeid shrimps, *Macrobrachium rosenbergii* and *Litopenaeus vannamei* and the inactivated specified pathogens comprise at least one of inactivated IHHNV (Infectious Hypodermal and Haematopoietic Necrosis Virus), Yellow head virus (YHV), IMNV (infectious myonecrosis virus), MrNV (*Macrobrachium rosenbergii* nodavirus), Taura syndrome virus (TSV) and/or WSSV (White spot syndrome virus).

* * * * *